United States Patent
Ma et al.

(10) Patent No.: US 11,371,003 B2
(45) Date of Patent: Jun. 28, 2022

(54) PHOTORECEPTOR SCAFFOLD FOR IN VITRO MODELING AND TRANSPLANTATION THERAPY

(71) Applicant: Wisconsin Alumni Research Foundation, Madison, WI (US)

(72) Inventors: Zhenqiang Ma, Middleton, WI (US); Yei Hwan Jung, Madison, WI (US); Michael Phillips, Stoughton, WI (US); David Gamm, Waunakee, WI (US); Shaoqin Gong, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 493 days.

(21) Appl. No.: 15/016,753

(22) Filed: Feb. 5, 2016

(65) Prior Publication Data

US 2017/0226459 A1    Aug. 10, 2017

(51) Int. Cl.
  *C12M 3/00* (2006.01)
  *C12M 1/00* (2006.01)
  *C12M 1/12* (2006.01)

(52) U.S. Cl.
  CPC ............ *C12M 25/14* (2013.01); *C12M 21/08* (2013.01); *C12M 23/20* (2013.01); *C12M 23/26* (2013.01); *C12M 23/30* (2013.01)

(58) Field of Classification Search
  CPC ...... C12M 21/08; C12M 23/20; C12M 23/26; C12M 23/30; C12M 25/14
  See application file for complete search history.

(56) References Cited

U.S. PATENT DOCUMENTS

| | | | |
|---|---|---|---|
| 2011/0004304 A1* | 1/2011 | Tao ................... | C12M 23/16 623/6.63 |
| 2013/0065795 A1* | 3/2013 | Allbritton ........... | C12M 23/12 506/26 |
| 2013/0189341 A1* | 7/2013 | Regatieri ........... | G01N 33/5073 424/426 |
| 2014/0178992 A1* | 6/2014 | Nakashima ......... | C12M 23/12 435/375 |

* cited by examiner

*Primary Examiner* — Lydia Edwards
(74) *Attorney, Agent, or Firm* — Stinson LLP

(57) ABSTRACT

Photoreceptor scaffolds and scaffold systems including the photoreceptor scaffolds are described herein. The scaffolds and scaffold systems can be used for transplantation of organized photoreceptor tissue, with or without RPE, which may improve grafted cell survival, integration, and functional visual rescue. Particularly, the photoreceptor scaffold is structured from a biocompatible film, patterned with an array of unique through-holes having a curvilinear cell receiver and at least one cell guide channel.

13 Claims, 9 Drawing Sheets

PHOTORECEPTOR SCAFFOLD FOR IN VITRO MODELING AND TRANSPLANTATION THERAPY

STATEMENT OF GOVERNMENT SUPPORT

This invention was made with government support under FA9550-09-1-0482 awarded by the USAF/AFOSR and CA166178 awarded by the National Institutes of Health. The government has certain rights in the invention.

BACKGROUND OF THE DISCLOSURE

The present disclosure relates generally to a photoreceptor scaffold for photoreceptor polarization and the use of the photoreceptor scaffold with a second scaffold in a scaffold system to generate a retinal pigment epithelium (RPE) and photoreceptor tissue construct. The scaffold systems can be used for in vitro developmental and disease studies, as well as for drug screening. These systems can further be used for transplantation of organized photoreceptor tissue with or without RPE, which may improve grafted cell survival, integration, and functional visual rescue.

Photoreceptors are the gatekeepers of vision, and they capture and transduce photons into electro-chemical signals to be processed by the retina and visual centers of the brain. Adjacent to the photoreceptors are the retinal pigment epithelium (RPE), supportive cells required for photoreceptor health and function. All blinding disorders of the outer retina involve dysfunction and eventual degeneration of the photoreceptors, either alone (as occurs in many forms of retinitis pigmentosa) or with involvement of the RPE (as found with the prevalent disorder, age-related macular degeneration (AMD)). Currently, these patients have limited to no treatment options. One broadly applicable treatment strategy would be to replace photoreceptors alone or in combination with RPE.

The only approved embryonic stem cell ("ESC") clinical trial currently underway in humans involves the transplantation of RPE via a simple, disorganized bolus injection of cells. While the work has demonstrated the safety of this approach, it lacks sufficient complexity to recapitulate the precise spatial orientation required for proper RPE function. Furthermore, transplanting RPE alone will not rescue vision in advanced disease. For this to occur, light sensing photoreceptors must also be replaced. To make this prospect more complex, photoreceptors are a highly polarized, specialized cell type with apical outer segments containing light sensing photopigments and basal axon terminals. While transplantation of polarized photoreceptors with or without RPE presents significant challenges, microfabrication technology offers potential solutions to these issues.

Particularly, it would be advantageous if a scaffold system could be prepared to provide polarization of photoreceptors, with or without RPE, to mimic native retinal tissues. It would be further advantageous if these systems could provide a means to transplant organized photoreceptor tissue, with or without RPE, which may improve grafted cell survival, integration, and functional visual rescue compared to simple bolus cellular injections.

BRIEF DESCRIPTION OF THE DISCLOSURE

The present disclosure is generally related to photoreceptor scaffolds and scaffold systems including the photoreceptor scaffolds that can be used for transplantation of organized photoreceptor tissue with or without RPE, which may improve grafted cell survival, integration, and functional visual rescue. Particularly, the photoreceptor scaffold is structured from a biocompatible film, patterned with an array of unique through-holes having a curvilinear cell receiver and at least one cell guide channel.

In one aspect, the present disclosure is directed to a scaffold comprising a cell support layer comprising at least one curvilinear cell receiver connected to at least one cell guide channel. The at least one curvilinear cell receiver connected to at least one cell guide channel extends through the cell support layer. The cell receiver comprises a diameter that is larger than the diameter of an opening in the cell guide channel.

In another aspect, the present disclosure is directed to a scaffold system comprising a first scaffold comprising a first cell support layer comprising at least one curvilinear cell receiver connected to at least one cell guide channel, and a second scaffold comprising a second cell support layer comprising at least one throughhole that extends through the second cell support layer. The at least one curvilinear cell receiver connected to at least one cell guide channel extends through the first cell support layer, and the cell receiver comprises a diameter that is larger than the diameter of an opening in the cell guide channel.

In another aspect, the present disclosure is directed to a cell culture scaffold system comprising a scaffold comprising a cell support layer comprising at least one curvilinear cell receiver connected to at least one cell guide channel and at least one cell in the cell support layer. The at least one curvilinear cell receiver connected to at least one cell guide channel extends through the first cell support layer. The cell receiver comprises a diameter that is larger than the diameter of an opening in the cell guide channel.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 2A is a line drawing of an exemplary scaffold of the scaffold system and FIG. 2B is a photograph of the exemplary scaffold of the scaffold system.

FIG. 6A depicts a schematic illustration of the fabrication process for the PR scaffold. A silicon wafer mold was formed using isotropic and anisotropic etching via a layer of photoresist mask. A second mold of hybrid PDMS was cured on the silicon mold and delaminated. s-PDMS was filled and cured in between the second mold and a silicon wafer to create the PR scaffold. FIG. 6B depicts a top view of the scaffold taken with SEM. FIG. 6C is a bottom view of the scaffold taken with SEM. FIG. 6D is a cross-section view of the scaffold taken with SEM. FIG. 6E depicts live cell staining (green), showing cell viability in the scaffold and characteristic photoreceptor protein expression. FIG. 6F depicts RCVRN recoverin in purple. FIGS. 6G & 6H show PRs extending out the through-holes shown by SEM at low (FIG. 6G) and high magnification (FIG. 6H). FIG. 6I is a schematic illustration of the fabrication process for the PR:RPE scaffold. Here, the cross-shaped posts on the RPE scaffold serve as structural support for the top PR.

DETAILED DESCRIPTION

Figure 1:
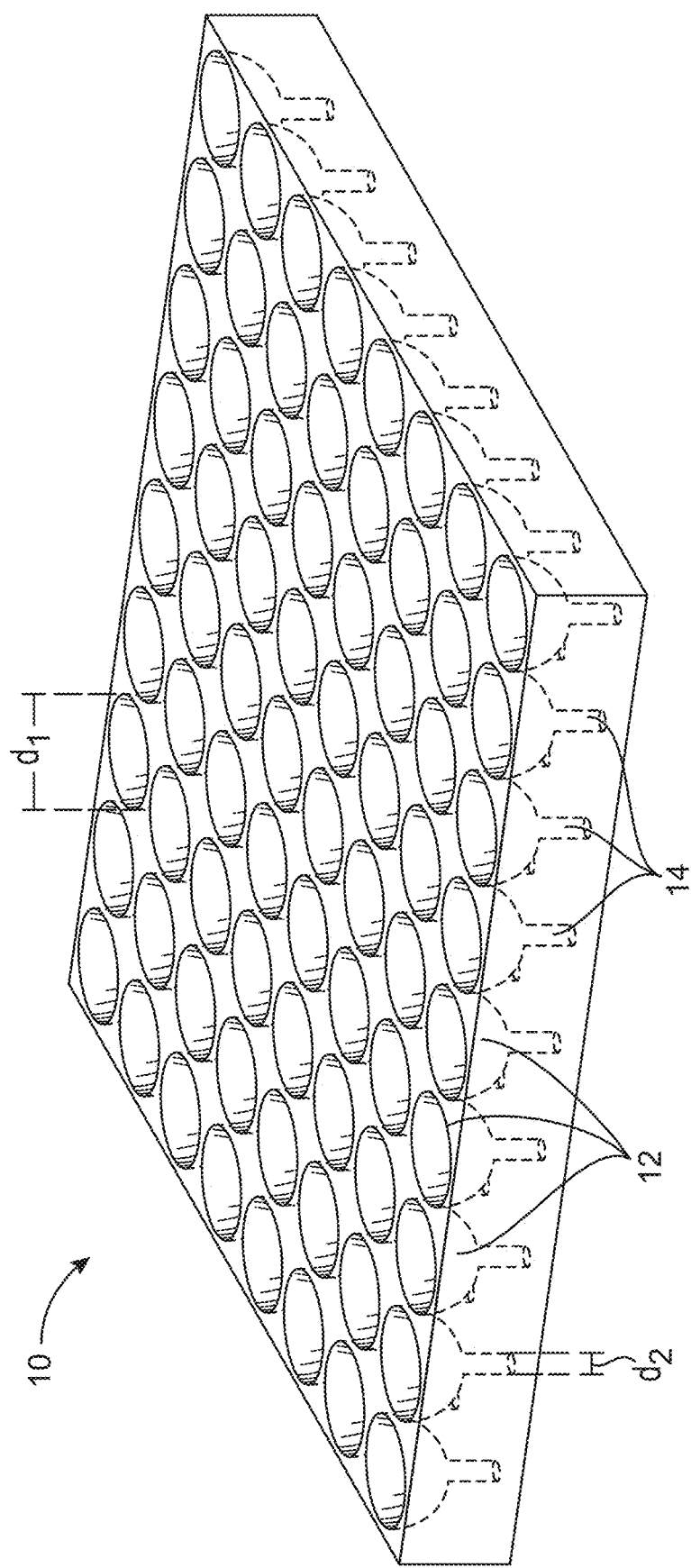
FIG. 1 depicts an isometric view of one exemplary scaffold of the scaffold system of the present disclosure.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The present disclosure is directed to a photoreceptor scaffold for photoreceptor polarization and the use of the photoreceptor scaffold with a second scaffold in a scaffold system to generate a retinal pigment epithelium (RPE) and photoreceptor tissue construct. The scaffold systems can be used for in vitro developmental and disease studies, as well as for drug screening. These systems can further be used for transplantation of organized photoreceptor tissue with or without RPE, which may improve grafted cell survival, integration, and functional visual rescue.

Structure of Scaffold and Scaffold System

Generally, a scaffold is provided for use in cell culture. The scaffold generally includes a cell support layer having at least one curvilinear cell receiver connected to at least one cell guide channel. The at least one curvilinear cell receiver connected to at least one cell guide channel extends through the cell support layer. The cell support layer is typically comprised of a biocompatible flexible polymer, and in some particularly suitable embodiments, the polymer is biodegradable. The polymer can be porous or non-porous. Suitable polymers include, but are not limited to, synthetic rubbers such as silicone rubbers (e.g., polydimethylsiloxane (PDMS)), polyurethane rubber, styrene butadiene rubber, and acrylonitrile butadiene rubber, natural rubbers (e.g., poly-cis-isoprene), thermoplastic elastomers (e.g., thermoplastic polyurethane, thermoplastic copolyester, thermoplastic polyamide), epoxies (e.g., SU-8), polyimides, polyurethanes, polyamides, polyesters (e.g., poly(lactic-co-glycolic acid) (PLGA), polylactic acid (PLA), polyglycolic acid (PGA), polycaprolactone (PCL), poly(glycerol sebacate) (PGS)), polysaccharides (e.g., chitosan), parylene, and combinations thereof. Advantageously, these polymers are "plastic-like" in that they are flexible upon application of an applied force, allowing for ease of transplantation and manipulation of the scaffold. In one particular aspect, the polymer is PDMS.

The cell support layer generally has at least one curvilinear cell receiver connected to at least one cell guide channel, the combination of the at least one curvilinear cell receiver connected to the at least one cell guide channel extends through the cell support layer. As used herein, "curvilinear cell receiver" refers to a cell receiver having a spherical shape, a conical shape, and the like, and combinations thereof. In one particular aspect, the cell receiver is half-spherical in shape. As used herein, "cell guide channel" refers to a channel that allows for guided growth of cells such as growth of the processes that will become the outer segment of a photoreceptor cell.

One particularly suitable cell support layer is shown in FIG. 1. As shown in FIG. 1, the cell support layer 10 includes a plurality of curvilinear cell receivers 12, each receiver 12 connected to a single cell guide channel 14. As used herein, a "plurality" refers to at least two of a curvilinear cell receiver and/or cell guide channel, including at least 3, including at least 4, including at least 5 or more of a curvilinear cell receivers and/or cell guide channels. While as shown, the cell support layer 10 includes a plurality of curvilinear cell receivers 12, it should be understood by one skilled in the art that the cell support layer can include less than the plurality of curvilinear cell receivers shown, including a single curvilinear cell receiver, or greater than the plurality of curvilinear cell receivers shown without departing for the scope of the present disclosure.

In one embodiment, the curvilinear cell receiver 12 includes a diameter, indicated at $d_1$, that is larger than the diameter of the cell guide channel 14, indicated at $d_2$. In particularly suitable embodiments, the diameter of the curvilinear cell receiver 12, $d_1$, ranges from about 8 μm to about 15 μm, including from about 10 μm to about 15 μm, and including about 15 μm. The diameter of the cell guide channel 14, $d_2$, typically ranges from about 1 μm to about 7 μm, including from about 3 μm to about 6 μm, and including about 5 μm.

When a plurality of curvilinear cell receivers are connected to cell guide channels, the individual curvilinear cell receivers are spaced apart by from about 0.1 μm to about 5 μm, including from about 0.5 μm to about 3 μm, and including about 1 μm.

It should be recognized by one skilled in the art that, in the case of using the scaffold for photoreceptor cells, the processes that will become the outer segments of the photoreceptor cells grow downward in the cell guide channels. The outer segment is the specialized structure of the photoreceptor that captures light with light sensitive opsin molecules (cone and rod opsin). Light is transduced into an electrochemical signal by the photoreceptor that is then processed and sent to the visual centers of the brain. Growing photoreceptors in a polarized manner recapitulates their normal orientation in vivo. Transplanting photoreceptors with outer segments arranged to contact the RPE will promote critical interactions between these two cell types, and should lead to enhanced integration of the cells and increased functional rescue of vision.

Further, the closer the curvilinear cell receivers (and thus, the closer the cultured photoreceptor cells), the more improved the visual acuity can potentially be once the scaffold is transplanted. Accordingly, in one embodiment, the cell support layer is composed of PDMS, wherein the diameter $d_1$ of the curvilinear cell receiver can be increased by stretching the cell support layer, and then allowing the curvilinear cell receiver to resume its original diameter upon removal of the stretching force. Particularly, with this embodiment, one or more cells are received by the curvilinear cell receiver in its stretched configuration. Once the stretching force is removed, the cells will be held within the cell receiver. Such an embodiment is advantageous as it allows the curvilinear cell receivers to be spaced closer together upon removal of the stretching force.

Further, as shown in FIG. 1, a single curvilinear cell receiver 12 is connected to a single cell guide channel 14. It should be understood that, in some suitable embodiments, a single curvilinear cell receiver 12 can be connected to more than one cell guide channel 14 without departing from the scope of the present disclosure. As used herein, "connected to" refers to the curvilinear cell receiver in contact with at least one cell guide channel such that cells received by the curvilinear cell receiver can move/grow between the cell receiver and the guide channel. Further, it should be understood that the combination of cell receiver and cell guide channel extend entirely through the cell support layer.

Typically, the cell support layer has a thickness ranging from about 20 μm to about 45 μm, including from about 22 μm to about 35 μm, and including about 25 μm.

In another embodiment, the cell support layer is treated and/or coated such to render the polymeric layer hydrophilic. Any methods known in the art for rendering flexible polymers hydrophilic can be used without departing from the scope of the present disclosure. For example, an oxygen plasma treatment on the surface of a polymer transforms the hydrophobic surface to hydrophilic surface by introducing polar functional groups, which yields a completely wettable surface. Accordingly, methods for surface treatment include, but are not limited to, oxygen plasma treatment, ultraviolet (UV) radiation, UV/ozone treatment, corona discharges, as well as certain types of polymer or co-polymer coatings as known in the art.

The present disclosure is further directed to a scaffold system including the scaffold described above in combination with a second scaffold. In one aspect, the second scaffold includes the cell support layer described above and generally having at least one curvilinear cell receiver connected to at least one cell guide channel, the combination of the at least one curvilinear cell receiver connected to the at least one cell guide channel extends through the cell support layer.

In another aspect, the second scaffold includes a second cell support layer that may be composed of the same or different polymers as described above. Suitably, the second scaffold is composed of a polymer selected from the group consisting of, by way of example only, synthetic rubbers such as silicone rubbers (e.g., polydimethylsiloxane (PDMS)), polyurethane rubber, styrene butadiene rubber, and acrylonitrile butadiene rubber, natural rubbers (e.g., poly-cis-isoprene), thermoplastic elastomers (e.g., thermoplastic polyurethane, thermoplastic copolyester, thermoplastic polyamide), epoxies (e.g., SU-8), polyimides, polyurethanes, polyamides, polyesters (e.g., poly(lactic-co-glycolic acid) (PLGA), polylactic acid (PLA), polyglycolic acid (PGA), polycaprolactone (PCL), poly(glycerol sebacate) (PGS)), polysaccharides (e.g., chitosan), parylene, and combinations thereof. In one particular aspect, the polymer is PDMS.

Figure 2A:
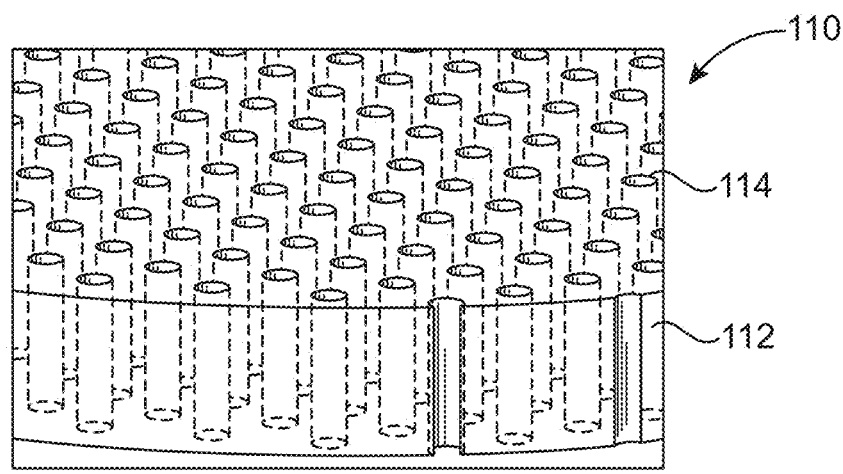
FIGS. 2A and 2B depict another exemplary scaffold of the scaffold system of the present disclosure. Particularly.
Figure 2B:
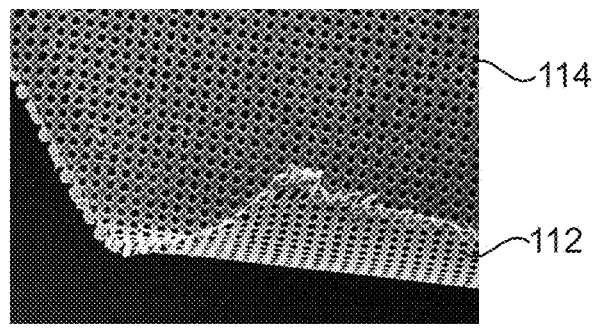

The second scaffold 110 includes at least one throughhole 114 that extends through the second cell support layer 112 (FIGS. 2A & 2B). The throughholes are typically included in the second scaffold to allow media and/or metabolites to flow in and out of the second scaffold. In suitable embodiments, the throughholes have a diameter of about 5 μm.

Typically, the second scaffold has a thickness of from about 20 μm to about 45 μm, including from about 22 μm to about 35 μm, and including about 25 μm.

Figure 3:
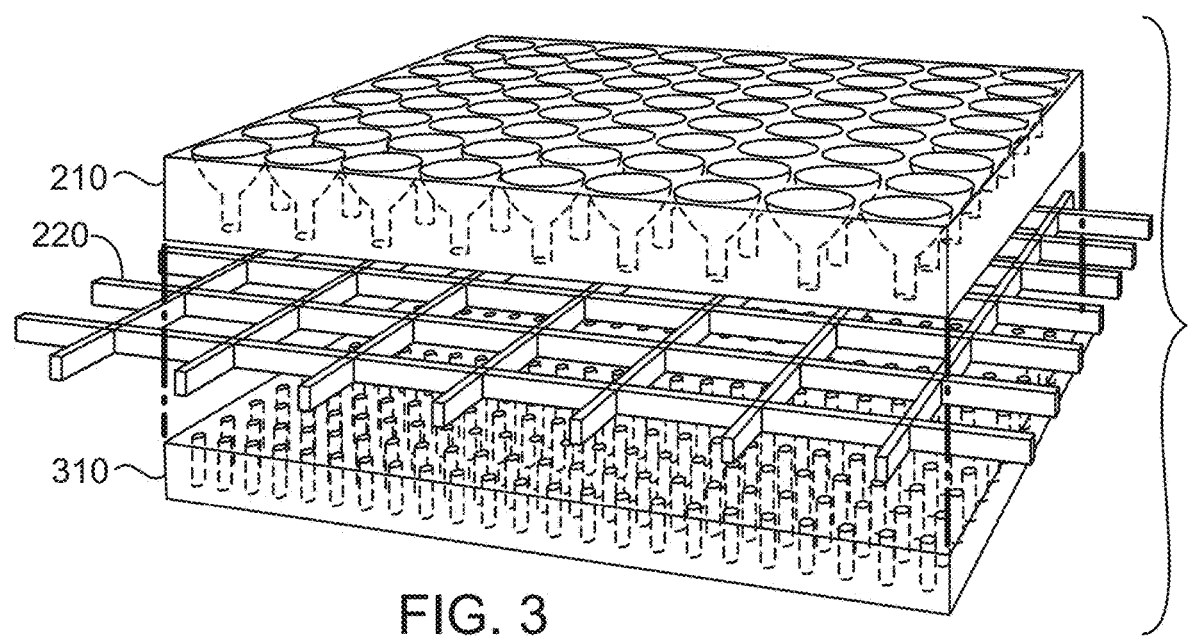
FIG. 3 depicts an exploded view of one exemplary scaffold system of the present disclosure.

In some embodiments, a support member is positioned between the first scaffold and the second scaffold (see FIG. 3). The support member 220 maintains space between the first scaffold 210 and the second scaffold 310 to allow for cell growth in a vertical direction from the first scaffold 210 and/or second scaffold 310. Typically, the space, s, between the first scaffold and the second scaffold ranges from about 2 μm to about 15 μm, including about 10 μm (see FIG. 4). This spacing allows the RPE layer to be housed in between the two layers, and to contact the photoreceptor outer segments exiting the bottom channels of the top layer.

Figure 5:
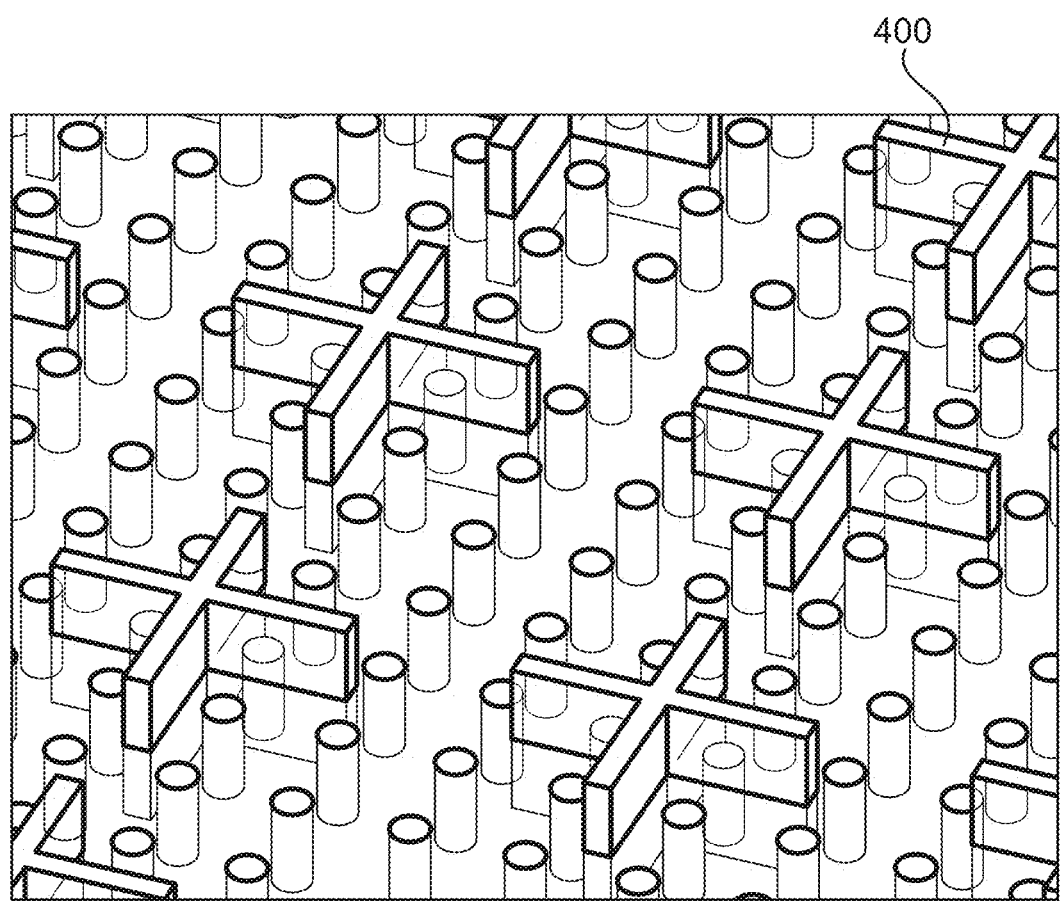
FIG. 5 depicts one exemplary scaffold system of the present disclosure, wherein the system includes a support member including a plurality of posts.
Figure 6A:
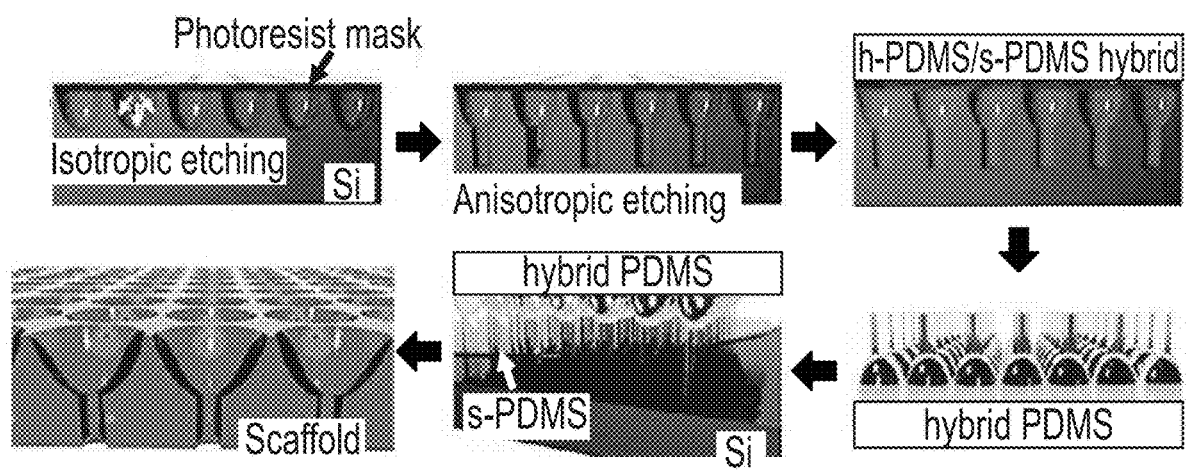
FIGS. 6A-6I depict a schematic illustration of the fabrication process for the scaffold system prepared in Example 1.
Figure 6B:
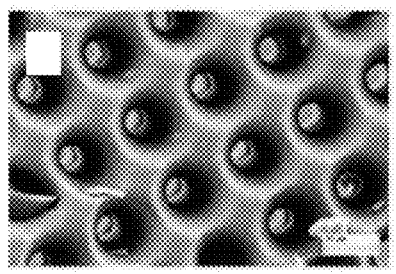
Figure 6C:
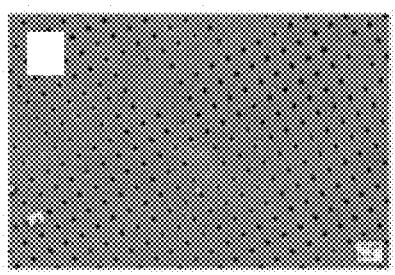
Figure 6D:
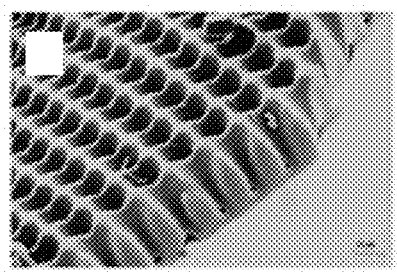
Figure 6E:
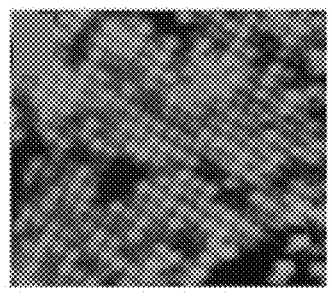
Figure 6F:
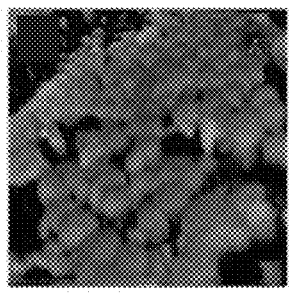
Figure 6G:
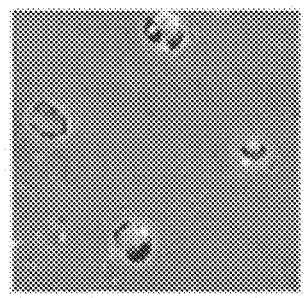
Figure 6H:
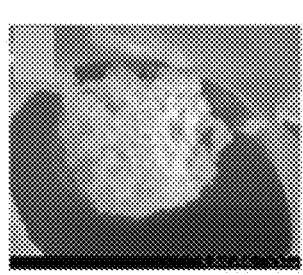
Figure 6I:
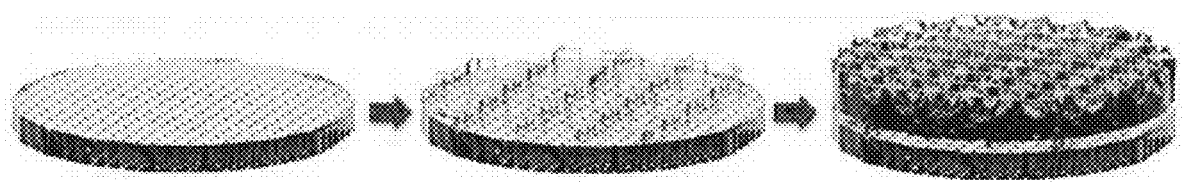

The support member may be any support member as known in the art. For example, in one embodiment, the support member is a cross-hatched insert as shown in FIG. 3. In another embodiment, the support member includes a plurality of posts 400 as shown in FIG. 5.

Methods of Preparing the Scaffold

The first and second scaffolds may be prepared by forming a polymeric mold for each cell support layer. For example, to prepare the first scaffold, a mold having microscale circular patterns is prepared using photolithography, plasma etching, and/or the like. More typically, the curvilinear cell receivers are prepared using isotropic plasma etching. The cell guide channels can be prepared using anisotropic plasma etching. The second scaffold may be prepared similarly to the first scaffold and throughholes are prepared using anisotropic plasma etching. A second mold is made using moldable polymers (e.g., PDMS), molded from the silicon mold, and the second mold is pressed with a bulk silicon wafer with a flat surface where PDMS (for the scaffold) is flowed into. While described herein as preparing the scaffolds using photolithography, plasma etching and molding, it should be understood that any means for preparing polymeric scaffolds as known in the art can be used without departing from the present disclosure. Other suitable methods include, for example, direct printing using a 3D printer or molding using a micro-injection molding machine.

To prepare the support member, an ultrathin polymer film is prepared using any method known in the art. Exemplary polymers for use as the support member include those listed above for the first and second scaffolds. In an alternative embodiment, a silicon wafer with negative (i.e., cliffs instead of bumps) patterns of support membrane is used in place of a flat silicon surface to mold one of the scaffolds during the molding process, creating a support member simultaneously on the surface of a scaffold.

Figure 4:
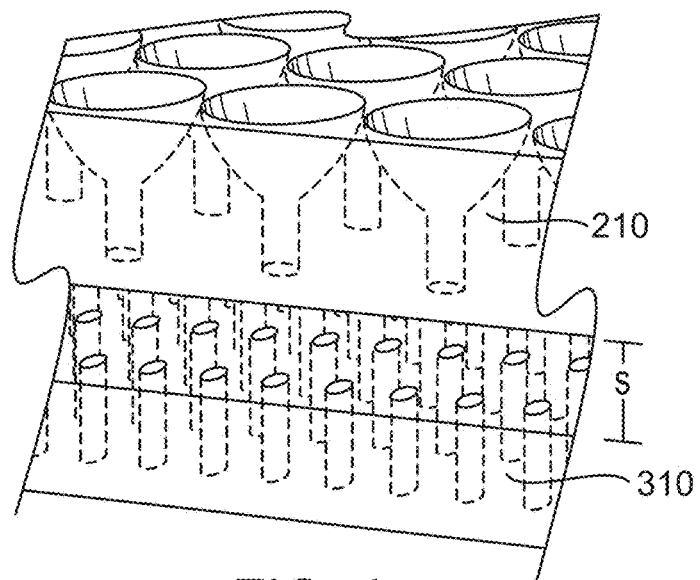
FIG. 4 depicts one exemplary scaffold system of the present disclosure.

To form the scaffold system, the first scaffold, with the support member, is laminated to the second scaffold without a support member. Chemical bonding as known in the art is then used to permanently bond the layers. An exemplary scaffold system is shown in FIG. 4. A micro hole punch can then be used to cut the scaffold system. The size of the hole punched using the micro hole punch will depend on the end use of the scaffold system. In particularly suitable embodiments, the micro hole punch allows for holes sized in diameter of from about 1 mm to about 5 mm Uses of the Scaffold System in Cell Culture Advantageously, the scaffolds and scaffold systems of the present disclosure can be used for cell culturing, transplantation, developmental modeling, disease modeling, and for drug screening.

When used for cell culture, the cell culture scaffold system generally includes a scaffold including a cell support layer. The cell support layer is typically comprised of a biocompatible flexible polymer, and in some particularly suitable embodiments, the polymer is biodegradable. The polymer may be porous or nonporous. Suitable polymers include, but are not limited to, synthetic rubbers such as silicone rubbers (e.g., polydimethylsiloxane (PDMS)), polyurethane rubber, styrene butadiene rubber, and acrylonitrile butadiene rubber, natural rubbers (e.g., poly-cis-isoprene), thermoplastic elastomers (e.g., thermoplastic polyurethane, thermoplastic copolyester, thermoplastic polyamide), epoxies (e.g., SU-8), polyimides, polyurethanes, polyamides, polyesters (e.g., poly(lactic-co-glycolic acid) (PLGA), polylactic acid (PLA), polyglycolic acid (PGA), polycaprolactone (PCL), poly(glycerol sebacate) (PGS)), polysaccharides (e.g., chitosan), parylene, and combinations thereof. In one particular aspect, the polymer is PDMS.

The cell support layer includes at least one curvilinear cell receiver connected to at least one cell guide channel, the at least one curvilinear cell receiver connected to the at least one cell guide channel extends through the cell support layer. The cell receiver is as described above. Particularly, the cell receiver has a diameter that is larger than the diameter of an opening in the cell guide channel.

As noted above, it should be understood by one skilled in the art that the cell support layer can include more than a single curvilinear cell receiver connected to a single cell guide channel Particularly, the cell support layer of the cell culture scaffold system may include a plurality of curvilinear cell receivers, each separately connected to one or more cell guide channels without departing for the scope of the present disclosure.

When a plurality of curvilinear cell receivers are connected to cell guide channels, the individual curvilinear cell receivers are spaced apart by from about 0.1 μm to about 5 μm, including from about 0.5 μm to about 3 μm, and including about 1 μm.

Typically, the cell support layer has a thickness ranging from about 8 μm to about 45 μm, including from about 12 μm to about 30 μm, and including about 20 μm.

In some embodiments, the cell support layer is treated and/or coated such to render the polymer hydrophilic as described above.

The cell culture scaffold of the present disclosure may include the scaffold described above in combination with a second scaffold. In one aspect, the second scaffold includes the cell support layer described above and generally having at least one curvilinear cell receiver connected to at least one cell guide channel, the combination of the at least one curvilinear cell receiver connected to the at least one cell guide channel extends through the cell support layer.

In another aspect, the second scaffold includes a second cell support layer that may be composed of the same or different polymers as described above. Suitably, the second scaffold is composed of a polymer selected from the group consisting of, by way of example only, synthetic rubbers such as silicone rubbers (e.g., polydimethylsiloxane (PDMS)), polyurethane rubber, styrene butadiene rubber, and acrylonitrile butadiene rubber, natural rubbers (e.g., poly-cis-isoprene), thermoplastic elastomers (e.g., thermoplastic polyurethane, thermoplastic copolyester, thermoplastic polyamide), epoxies (e.g., SU-8), polyimides, polyurethanes, polyamides, polyesters (e.g., poly(lactic-co-glycolic acid) (PLGA), polylactic acid (PLA), polyglycolic acid (PGA), polycaprolactone (PCL), poly(glycerol sebacate) (PGS)), polysaccharides (e.g., chitosan), parylene, and combinations thereof. In one particular aspect, the polymer is PDMS.

The second scaffold includes at least one throughhole that extends through the second cell support layer. The throughholes are typically included in the second scaffold to allow media and/or metabolites to flow in and out of the second scaffold. In suitable embodiments, the throughholes have a diameter of about 5 μm.

Typically, the second scaffold has a thickness of from about 3 μm to about 25 μm, including from about 5 μm to about 15 μm, including from about 5 μm to about 10 μm, and including about 8 μm.

In some embodiments, there is a support member as described above positioned between the first scaffold and the second scaffold. The support member maintains space between the first scaffold and the second scaffold to allow for cell growth in a vertical directed from the first scaffold and/or second scaffold. Typically, the space between the first scaffold and the second scaffold ranges from about 2 μm to about 5 μm, including about 10 μm.

The cell culture scaffold system further includes at least one cell in one or both of the first and second cell support layers. Cells received by the curvilinear cell receiver of the first cell support layer can move/grow between the cell receiver and the guide channel of the first cell support layer. Any cells as known in the art for use in a scaffold system for in vitro developmental and disease studies, as well as for drug screening, could be used with the cell culture scaffold system of the present disclosure. Particularly, suitable cells include photoreceptor cells, retinal pigment epithelium (RPE) cells, bipolar cells, ganglion cells, and combinations thereof.

Use of the cell culture scaffold system results in the formation of an organized multi-cellular construct that mimics the cellular structure and organization observed in vivo, allowing for improved grafted cell survival, integration, and functional visual rescue. Further, these structures prevent reflux similar to currently found with the use of bolus injections.

More particularly, in one suitable embodiment, the first scaffold includes at least one photoreceptor cell in the first cell support layer and the second scaffold includes at least one retinal pigment epithelium (RPE) cell in the second cell support layer. Photoreceptors are the gatekeepers of vision, and they capture and transduce photos into electro-chemical signals to be processed by the retina and visual centers of the brain. Photoreceptors are a highly polarized, specialized cell types with apical outer segments containing light sensing photo-pigments and basal axon terminals. As naturally found, adjacent to the photoreceptors are the RPE cells, supportive cells required for photoreceptor health and function. Particularly, an RPE monolayer provides cellular and structural cues for photoreceptor polarization. In this embodiment, once placed, the photoreceptors can start to grow their process, which will ultimately become their outer segments through the cell guide channel(s) towards the RPE. These polarized photoreceptors are then poised for in vitro testing or transplantation.

When used for transplantation, the cell culture scaffold system as described above is used to culture the cells to form a construct and then the cultured construct is transplanted to the eye of a subject using standard vitreoretinal surgical techniques. Suitable diseases and/or conditions that these constructs could be potentially used for include all inherited or acquired diseases or retinal injuries involving dysfunction and/or death of the RPE and/or photoreceptors. These include, but are not limited to, age-related macular degeneration ("dry" or "wet" AMD), retinitis pigmentosa, retinal detachment, cone dystrophies, cone-rod dystrophies, Usher's syndrome, Best's disease, choroideremia, gyrate atrophy, myopic degeneration, sorsby's fundus dystrophy, doyne honeycomb macular dystrophy, and Stargardt's macular dystrophy.

When the scaffold system is used for drug screening, candidate agents are added to a culture media. Cell health and survival can then be assessed using standard techniques. Additionally, the scaffold system makes it possible to examine the effects of candidate agents on cellular structures that do not typically develop without the aid of this scaffold system, such as the development of photoreceptor outer segments. Many blinding retinal disorders originate in the photoreceptor outer segment, involving an absence of photoreceptor specific protein expression, misfolded proteins, incorrect packaging of proteins, or ectopic localization of these proteins within the photoreceptor. These components of disease and potential candidates are difficult to assess in a typical two-dimensional culture system (cells grown on a flat surface). Furthermore, many diseases require modeling of RPE-photoreceptor interactions. Investigating these interactions is possible with this system, but not with traditional two-dimensional culture, as RPE and photoreceptors will not grow on top of each other in a two dimensional culture.

EXAMPLES

Example 1

In this Example, a scaffold system of the present disclosure was prepared.

Photoreceptor (PR) Scaffold

The fabrication process of the photoreceptor scaffold was initiated by creating the first silicon wafer based mold. On a bulk single crystalline silicon wafer (3 cm×3 cm) with (100) orientation, an etch mask with an array of micro-scale circular shape holes having a diameter of 5 µm that were spaced apart by 16 µm from center to center was patterned using an AZ5214 photoresist based negative photolithography process. The patterned silicon wafer was etched using a reactive ion etcher with a gas mixture of $SF_6$ and $O_2$ at 15 W of power for 2 hours to achieve isotropic etching of the holes. This created arrays of bowl shaped (i.e., half-spherical) etch profiles 15 µm in diameter and 12 µm in depth, spaced apart by 1 µm, edge to edge.

Using the same etch mask, a Bosch process was followed next using a deep reactive ion etcher for steep-sided holes with a high anisotropic etch profile. The depth of the vertical, steep-sided holes was 13 µm. The etched silicon wafer was immersed in a photoresist stripper (AZ400T) for 24 hours and treated with oxygen plasma, followed by plasma deposition of a Teflon film. Hard (h-) PDMS was prepared by mixing 3.4 g vinyl prepolymer, 18 µl platinum catalyst, 60 µl modulator 2,4,6,8-tetramethyltetravinylcyclotetrasiloxane, and 1 g hydroprepolymer, which was degassed and spin-coated on the silicon mold at 2,000 rpm for 30 seconds. The silicon mold with h-PDMS was partially cured in 60° C. oven for 10 minutes. Thereafter, 25 g of soft (s-) PDMS (siloxane:curing agent=4:1) was poured and cured over the mold inside a petri-dish with a diameter of 3 inches. After 24 hours of curing at 70° C., the hybrid (h- and s-) PDMS was delaminated slowly from the silicon mold. The hybrid PDMS mold was treated with trichlorosilane using vacuum evaporation for 6 hours and rinsed with de-ionized water and dried. On a Teflon coated bulk silicon wafer, a drop of s-PDMS (siloxane:curing agent=4:1) was pressed using the hybrid PDMS mold with a 60 g weight and cured in vacuum oven for 24 hours. Finally, the cured s-PDMS scaffold was delaminated from the hybrid PDMS mold and mounted on the transwell snap with a PDMS based adhesive for cell culturing.

RPE Scaffold

The fabrication process of the RPE scaffold was identical to the above photoreceptor scaffold fabrication method, with exclusions of certain steps to create the bowl shapes in the silicon mold. The circular array was much denser (5 µm in diameter spaced apart by 10 µm from center to center). The hybrid PDMS mold was also replaced with pure s-PDMS mold. Moreover, the structural posts were created by pressing the PDMS drop with the s-PDMS mold on a negatively structured silicon wafer instead of bulk silicon wafer. The negatively structured silicon wafer was created by patterning either cross-shaped structures or circles that are spaced apart by 48 µm, center to center using AZ5214 photoresist. A Bosch process was used to etch the patterned silicon wafer and the wafer was cleaned with AZ400T stripper, treated with oxygen plasma, and coated with Teflon.

To bond the two scaffolds, the backside (vertical throughhole side) of the photoreceptor scaffold was exposed with UV/ozone for 1 minute with 0.5 L/min of $O_2$. Immediately after the exposure, the RPE scaffold with structural posts was laminated on the exposed photoreceptor scaffold.

The fabrication process for the scaffold system prepared in this Example is shown in FIGS. 6A-6I.

Example 2

In this Example, an alternative method to create a RPE scaffold was developed. Particularly, a parylene-based RPE scaffold was prepared.

10 µm of parylene C was coated using chemical vapor deposition on a 4-inch silicon wafer and an array of dense circular posts having a diameter of 5 µm that are spaced apart by 10 µm from center to center was patterned with an AZ5214 photoresist, followed by deposition of 150 nm of copper using an electron-beam evaporator. The wafer was immersed in acetone in order to remove circular posts thereby exposing the circular holes. Using copper as an etch mask, the parylene film was etched using a reactive ion etcher with $O_2$ gas, at 200 W of power for 50 minutes. Copper was completely removed using ammonium persulfate and the parylene film with vertical holes was delaminated from the silicon wafer and mounted on the transwell snap for cell culturing.

What is claimed is:

1. A scaffold comprising a single cell support layer comprising at least one curvilinear cell receiver in physical contact with at least one cell guide channel, the at least one curvilinear cell receiver in physical contact with at least one cell guide channel extends through the cell support layer, the cell receiver comprising a diameter that is larger than the diameter of an opening in the cell guide channel, wherein the cell support layer comprises one or more of a biocompatible flexible polymer and a biodegradable flexible polymer, wherein the at least one curvilinear cell receiver has a diameter ranging from about 8 µm to about 15 µm, and wherein the at least one cell guide channel has a diameter of about 5 µm.

2. The scaffold of claim 1 wherein the cell support layer comprises a biocompatible flexible polymer.

3. The scaffold of claim 1 wherein the biocompatible flexible polymer is selected from the group consisting of silicone rubber, polyurethane rubber, styrene butadiene rubber, and acrylonitrile butadiene rubber, natural rubber, thermoplastic elastomer, epoxy, polyimide, polyurethane, polyamide, polyester, polysaccharide, parylene, and combinations thereof.

4. The scaffold of claim 1 wherein the cell support layer comprises a biodegradable flexible polymer.

5. The scaffold of claim 1 wherein the cell support layer comprises at least a first curvilinear cell receiver and a second curvilinear cell receiver, the first curvilinear cell receiver spaced about 1 µm apart from the second curvilinear cell receiver.

6. The scaffold of claim 1 wherein the curvilinear cell receiver is in physical contact with at least a first cell guide channel and a second cell guide channel.

7. The scaffold of claim 1, wherein the single cell support layer comprises at least one photoreceptor cell.

8. A scaffold system comprising a first scaffold comprising a first cell support layer comprising at least one curvilinear cell receiver in physical contact with at least one cell guide channel, the at least one curvilinear cell receiver in physical contact with at least one cell guide channel extends through the first cell support layer, the cell receiver comprising a diameter that is larger than the diameter of an opening in the cell guide channel, and a second scaffold comprising a second cell support layer comprising at least one throughhole that extends through the second cell support layer, wherein at least one of the first cell support layer and the second cell support layer comprises one or more of a biocompatible flexible polymer and a biodegradable flexible polymer, wherein the at least one curvilinear cell receiver has a diameter ranging from about 10 µm to about 15 µm, wherein the at least one cell guide channel has a diameter of about 5 µm.

9. The scaffold system of claim 8 wherein at least one of the first cell support layer and the second cell support layer comprises a biocompatible flexible polymer selected from the group consisting of silicone rubber, polyurethane rubber, styrene butadiene rubber, and acrylonitrile butadiene rubber, natural rubber, thermoplastic elastomer, epoxy, polyimide, polyurethane, polyamide, polyester, polysaccharide, parylene, and combinations thereof.

10. The scaffold system of claim 8 wherein at least one of the first cell support layer and the second cell support layer comprises a biodegradable flexible polymer.

11. The scaffold system of claim 8 wherein the first cell support layer comprises at least a first curvilinear cell receiver and a second curvilinear cell receiver, the first curvilinear cell receiver spaced about 1 µm apart from the second curvilinear cell receiver.

12. The scaffold system of claim 8 where a support member is positioned between the first scaffold and the second scaffold.

13. The scaffold system of claim 8, wherein the first cell support layer comprises a photoreceptor cell and the second cell support layer comprises a retinal pigment epithelial cell.

* * * * *